United States Patent [19]

Voelskow et al.

[11] Patent Number: 4,745,059

[45] Date of Patent: May 17, 1988

[54] PROCESS FOR THE PREPARATION OF L-PHENYLALANINE

[75] Inventors: Hartmut Voelskow, Hattersheim am Main; Reinhold Keller, Bad Soden am Taunus; Merten Schlingmann, Königstein; Martin Platen, Frankfurt am Main; Johann Then, Bonn; Gerhard Wöhner, Flörsheim am Main, all of Fed. Rep. of Germany

[73] Assignee: Hoechst Aktiengesellschaft, Fed. Rep. of Germany

[21] Appl. No.: 749,465

[22] Filed: Jun. 27, 1985

[30] Foreign Application Priority Data

Jun. 29, 1984 [DE]  Fed. Rep. of Germany ....... 3423936

[51] Int. Cl.$^4$ .................... C12P 13/22; C12N 11/04; C12N 1/36
[52] U.S. Cl. .................................. 435/108; 435/245; 435/182
[58] Field of Search ................ 435/108, 253, 182, 245

[56] References Cited

U.S. PATENT DOCUMENTS

| | | | |
|---|---|---|---|
| 3,660,235 | 5/1972 | Okumura et al. | 435/108 |
| 4,518,692 | 5/1985 | Rozzell | 435/108 |
| 4,525,454 | 6/1985 | Rozzell | 435/106 |
| 4,542,069 | 9/1985 | Mauz et al. | 428/402 |
| 4,600,692 | 7/1986 | Wood et al. | 435/108 |
| 4,603,111 | 7/1986 | Keller et al. | 435/182 |

FOREIGN PATENT DOCUMENTS

| | | | |
|---|---|---|---|
| 0135846 | 4/1985 | European Pat. Off. | 435/106 |
| 0152275 | 6/1985 | European Pat. Off. | 435/108 |
| 0151488 | 8/1985 | European Pat. Off. | 435/108 |
| 2152503 | 12/1984 | United Kingdom | 435/108 |

OTHER PUBLICATIONS

Keller, B. et al. *Biol Abstr.* 77(3)2460 1984.
Bulot, E. et al. *Chemical Abstracts* 102:147439h, 1985.

*Primary Examiner*—Elizabeth Weimar
*Attorney, Agent, or Firm*—Finnegan, Henderson, Farabow, Garrett & Dunner

[57] ABSTRACT

L-Phenylalanine can be prepared using microorganisms belonging to the series comprising *E. coli, Paracoccus denitrificans, Torula, Rhodotorula* or *Streptomyces* after adaptation to phenylpyruvic acid, by amination with suitable sources of nitrogen. It is advantageous to employ the microorganism in the form of fixed cells.

6 Claims, No Drawings

PROCESS FOR THE PREPARATION OF L-PHENYLALANINE

Phenylalanine is an aminoacid which occurs in every living organism. Most bacteria and fungi, including yeasts, synthesize and phenylalanine necessary for growth themselves. However, the enzyme systems required for this purpose only exist at such a low activity that no more phenylalanine is formed than the precise amount required by the cell.

The slowest stages in the biosynthesis of phenylalanine are the building-up of the aromatic ring. Attempts have, therefore, already been made to convert aromatic precursors into phenylalanine by bio-transformation using Rhodotorula yeasts or E. coli. However, the yields were so low that they were unsuitable for industrial production.

It has already been suggested (German Offenlegungsschrift 3,427,495, not previously published) to prepare L-amino acids from α-keto acids by adding the desired α-keto acid to microorganisms during the logarithmic growth phase. Phenylpyruvic acid is converted into L-phenylalanine in this way by Brevibacterium.

However, phenylpyruvic acid has a toxic effect on many microorganisms, inter alia also on those employed in accordance with the invention. It was therefore surprising that it has been possible to select, by adaptation to increasing amounts of phenylpyruvic acid, microorganisms which produce up to about 15 g of L-phenylalanine per liter of culture medium by means of this precursor.

The invention relates, therefore, to a process for the preparation of L-phenylalanine from phenylpyruvic acid and a source of nitrogen for the amination, by means of microorganisms, which comprises adapting a microorganism belonging to the series comprising *E. coli*, *Paracoccus denitrificans*, Torula, Rhodotorula or Streptomyces to phenylpyruvic acid or to a phenylpyruvate.

Preferred strains of microorganisms are *E. coli* ATCC e 11,303, *Paracoccus denitrificans* DSM 65, *Rhodotorula glutinis* DSM 70,398 and various Streptomycetes isolated from samples of soil.

The adaptation of suitable strains is effected by repeated addition of a constant amount or by the addition of increasing amounts of phenylpyruvic acid to the appropriate culture media. Before or during the selection with respect to this aromatic starting material, it can be advantageous to carry out a mutation of the microorganisms by methods which are known per se, in order to accelerate the adaptation. By this means and by optimizing the media and growth conditions used, it is possible to raise the yields of phenylalanine originally achieved from a customary level of about 0.01 to 0.5 g/l, in special cases up to about 2.4 g, to a level of up to 15 g/l.

The microorganisms are advantageously employed in a fixed form. The known processes, advantageously the methods according to U.S. Pat. Nos. 4,603,111 3,243,591 and the processes mentioned therein are suitable for the fixing operation. The biocatalysts thus immobilized can be employed in a reactor working on the loop principle, in particular in an airlift reactor, as suggested in German Offenlegungsschrift 3,247,214.

The preferred nitrogen source is urea and ammonia in the form of its salts, in particular salts of monocarboxylic and polycarboxylic acids, as well as amino acids, in particular glycine, asparagine, aspartic acid, glutamine or glutamic acid.

Phenylpyruvic acid can be employed in the form of the free acid or suitable salts (depending on the medium used). Addition of these can be effected at the commencement of the inoculated culture of microorganisms or after a growth phase of about 10 to 90 hours, preferably 24 to 48 hours, in an amount of about 0.1 to 2%, relative to the weight of the medium. This result is also surprising, since, according to German Offenlegungsschrift 3,427,495, the best yield is associated with adding the α-keto acid during the logarithmic growth phase. Relative to the nitrogen source, the phenylpyruvic acid is employed in an amount slightly below stoichiometric equivalents. The cultures are incubated with these starting materials for about a further 10 to 90 hours, preferably 12 to 48 hours, in each case to match the strains employed. The starting materials can also be employed in a lower concentration, for instance 0.02 to 0.5%, during the growth phase, after which further addition in the amount indicated above is effected towards the end of, or after, the growth phase, for instance in the course of 24 to 48 hours. The most advantageous procedure for a particular strain can be determined in simple preliminary tests.

The addition of fumaric acid or salts thereof to the fermentation medium has a favorable effect on the conversion of phenylpyruvic acid into L-phenylalanine. It is particularly advantageous to add the ammonium salt, since the ammonium ions can then act as a nitrogen donor for the reaction.

The optimization of the media and growth conditions used, for example the pH, oxygen supply, temperature, concentrations of starting materials and, if appropriate, fixing conditions, can also be effected easily by means of simple preliminary tests.

The free cells cultured by the process according to the invention can be immobilized, and they then produce L-phenylalanine in a good space-time yield if nutrient solution is added continuously. A preferred embodiment is immobilization in the batch system when the L-phenylalanine synthesis is complete. It is then possible additionally to synthesize continuously up to about 10 g of phenylalanine per l of nutrient solution for a prolonged period.

In the following examples, percentages relate to weight.

EXAMPLE 1

*Escherichia coli* ATCC e 11,303 was mutated in a manner known per se by means of N-methyl-N'-nitro-N-nitrosoguanidine. The treated cells were introduced in the form of a 3% strength inoculum into 100 ml of adaptation medium of the composition:

1.5% of fumaric acid,
2.0% of meat extract,
0.05% of $MgSO_4.7H_2O$,
1.75% of ammonia,
0.2% of $KH_2PO_4$ and increasing amounts of phenylpyruvate and aspartic acid, and were incubated for 48 hours on a shaking machine at a pH of 7.5 and a temperature of 37° C. The cultures were inoculated several times, the amounts of phenylpyruvate and aspartic acid being increased in accordance with the figures given in Table 1.

TABLE 1

| Number of inoculations | Amount added [g] | |
|---|---|---|
| | phenylpyruvate | aspartic acid |
| first inoculation | 5 | 4 |
| second inoculation | 10 | 7 |
| third inoculation | 16 | 10 |
| forth inoculation | 24 | 20 |

The cultures were then diluted with physiological sodium chloride solution by a factor of $10^5$ to $10^6$ and were plated out on plates containing a medium of the above composition, including also 16 g/l of aspartic acid, 24 g/l of phenylpyruvate and 15 g/l of agar. Well-grown, large colonies were selected after incubation at 37° C. for a period of 1 to 2 days. Inter alia, the mutants *Escherichia coli* E-196 and *Escherichia coli* E-197 were isolated in this manner.

EXAMPLE 2

Cultures of *E. coli* ATCC e 11,303 mutated and selected in accordance with Example 1, and also the wild strain as a control, were inoculated into 100 ml of the following medium:
- 1.5% of fumaric acid,
- 2.0% of meat extract,
- 0.05% of $MgSO_4.7H_2O$,
- 1.75% of ammonia,
- 0.2% of $KH_2PO_4$,
- 0.7% of aspartic acid and
- 1% of phenylpyruvic acid, in the form of the Na salt, and
- 0.01% of $CaCl_2.2H_2O$.

A similar culture was made up from this after 2 days using 3% of inoculum and this was done twice further, in each case after 2 days. The cultures were incubated at 37° C. on a shaking machine. A new batch of 4 l from the last culture, divided amongst 8 conical flasks (2 l overall volume), each holding 500 ml, was inoculated with the same medium and incubated at 37° C. The phenylalanine contents stated in Table 2 were reached after 2 days.

TABLE 2

| Microorganism | phenylalanine in the medium (g/l) |
|---|---|
| *E. coli* E-196 | 9.3 |
| *E. coli* E-197 | 7.5 |
| *E. coli* ATCC e 11,303 (wild strain) | 2.4 |

A phenylalanine content of 15 g/l was achieved by increasing the concentration of phenylpyruvate to 1.7% and the concentration of aspartic acid to 1%. The cells were harvested by centrifuging after 2 days and were immobilized by the process of U.S. Pat. No. 4,603,111, Example 1.

EXAMPLE 3

A culture of *Paracoccus denitrificans* DSM 65, selected in accordance with the invention, was inoculated by means of an inoculation loop from an agar slant culture into 100 ml of the following medium:
- 1% of glucose,
- 0.4% of casein peptone,
- 0.4% of meat extract,
- 0.05% of yeast extract,
- 0.05% of liver extract,
- 0.25% of sodium chloride and
- 0.15% of $MgSO_4.7H_2O$.

The culture was inoculated at 30° C. in a conical flask (overall volume 300 ml) on a shaking machine. After 2 days, a laboratory fermenter of capacity 10 l was inoculated therefrom with the same medium. After a growth time of 24 hours at 500 r.p.m. and 10 l of air per minute and a temperature of 30° C., 50 g of glycine and 50 g of phenylpyruvate were added. After two further days the culture reached an optical density (extinction at 580 nm) of 6.2. 56% of the phenylpyruvate was thus converted into phenylalanine.

The culture was harvested by centrifuging, and the cells were immobilized by the process of U.S. Pat. No. 4,603,111, Example 2.

EXAMPLE 4

50 isolates of Streptomyces sp. from samples of soil were each inoculated into 100 ml portions of the following medium:
- 2% of soya flour,
- 2% of mannitol,
- 0.5% of phenylpyruvic acid, in the form of the Na salt, and
- 0.5% of aspartic acid.

Additionally, the strains were inoculated into 100 ml of a similar medium containing glycine instead of the aspartic acid. The cultures were inoculated at 30° C. on a shaking machine for 5 days. Samples were taken after 3 and 5 days. 7 strains from the cultures tested converted phenylpyruvate into phenylalanine in a yield of 30% to 60%, and these were therefore suitable for further adaptation.

EXAMPLE 5

100 g of the immobilized cells obtained in accordance with Example 2 were put into a glass column controlled thermostatically at 30° C., and a substrate solution of the following composition:
- 16 g/l of phenylpyruvic acid, in the form of the Na salt,
- 10 g/l of L-aspartic acid,
- 10 mg/l of $MgSO_4.7H_2O$ and
- 2 mg/l of pyridoxal phosphate was added. A concentration of 9.8 g/l of L-phenylalanine was reached at a flow rate of 50 ml/hour, a pH of 7.5 and a temperature of 30° C. In the course of this, oxalacetic acid which was liberated was decarboxylated to give pyruvic acid to the extent of about 50%. After removing water by distillation, the solution of product was concentrated to about one half, the pH value was adjusted to 5.5, and the L-phenylalanine was induced to crystallize by cooling to 5° C.

EXAMPLE 6

100 g of the immobilized cells obtained in accordance with Example 2 were put into a glass column thermostatically controlled at 30° C. A substrate solution of the following composition:
- 10 g/l of phenylpyruvic acid, in the form of the Na salt,
- 10 g/l of ammonium fumarate,
- 10 mg/l of $MgSO_4.7H_2O$ and
- 2 mg/l of pyridoxal phosphate was pumped through the column at a pH of 8.0 and at 30° C., at a flow rate of 20 ml/hour. In the course of this 9.7 g/l of L-phenylalanine were formed. The L-phenylalanine was obtained in a state of high purity by concentrating and crystallizing in accordance with Example 5.

EXAMPLE 7

100 g of the cells obtained in accordance with Example 2 were stirred with 80 ml of 8% strength sodium alginate solution, and the mixture was added dropwise through a jet into a crosslinking bath consisting of 0.5M calcium chloride solution. The resulting beads were filtered off, put into a glass column and treated in accordance with Example 5 with a substrate solution. 9.8 g/l of L-phenylalanine were obtained at a flow rate of 70 ml/hour.

EXAMPLE 8

100 g of the immobilized cells obtained in accordance with Example 3 were put into a glass column thermostatically controlled at 30° C., and a substrate solution of the following composition:

10 g/l of phenylpyruvic acid,
5 g/l of glycine,
10 mg/l of $MgSO_4.7H_2O$ and
3 mg/l of pyridoxal phosphate was added. 9.6 g/l of L-phenylalanine were obtained at a pH value of 7.0 and a flow rate of 20 ml/hour.

We claim:

1. A process for increasing the yield from the microbial preparation of L-phenylalanine comprising the step of adapting a microorganism from the group consisting of *E. coli, Paracoccus denitrificans,* Torula, Rhodotorula, and Streptomyces to tolerate increasing concentrations of a precursor selected from the group consisting of phenylpyruric acid and the salts thereof by repeated exposure to a constant or increasing amount of said precursor wherein said precursor is aminated in the presence of a nitrogen source in a nutrient solution by biotransformation so as to produce L-phenylalanine with said adapted microorganism.

2. The process as claimed in claim 1, wherein said microorganism is treated with a mutating agent before or during the adaption of the microorganism to said precursor.

3. The process as claimed in claim 1, wherein the nitrogen source employed is glycine, asparagine, aspartic acid, glutamine, glutamic acid or a monocarboxylic or polycarboxylic acid salt of ammonia.

4. The process as claimed in claim 1, wherein the microorganism is selected with respect to increasing amounts of phenylpyruvic acid or its salt.

5. The process as claimed in claim 1, wherein the microorganism is employed in the form of immobilized cells.

6. The process as claimed in claim 1, wherein fumaric acid or salts thereof are added to the nutrient solution in which the conversion to phenylalanine is carried out.

* * * * *